US008475818B2

(12) United States Patent
Guerino et al.

(10) Patent No.: US 8,475,818 B2
(45) Date of Patent: Jul. 2, 2013

(54) LOCAL TOPICAL ADMINISTRATION FORMULATIONS CONTAINING INDOXACARB

(75) Inventors: Frank Guerino, Monroe Township, NJ (US); Keith Alan Freehauf, Stockton, NJ (US); Roger Mervyn Sargent, Camden (AU); Peter Andrew O'Neil, Kirkham (AU); Robert D. Simmons, Martinsville, NJ (US); Chen-Chao Wang, West Windsor, NJ (US)

(73) Assignee: E. I. de Pont de Nemours and Company, Wilmington, DE (US)

( * ) Notice: Subject to any disclaimer, the term of this patent is extended or adjusted under 35 U.S.C. 154(b) by 799 days.

(21) Appl. No.: 12/439,351

(22) PCT Filed: Aug. 30, 2007

(86) PCT No.: PCT/US2007/019096
§ 371 (c)(1),
(2), (4) Date: Nov. 10, 2009

(87) PCT Pub. No.: WO2008/030385
PCT Pub. Date: Mar. 13, 2008

(65) Prior Publication Data
US 2010/0099668 A1    Apr. 22, 2010

Related U.S. Application Data

(60) Provisional application No. 60/841,846, filed on Sep. 1, 2006.

(51) Int. Cl.
*A01N 37/10* (2006.01)
*A01N 37/42* (2006.01)
*A01N 37/44* (2006.01)

(52) U.S. Cl.
USPC ......... 424/405; 514/229.2; 514/403; 514/531

(58) Field of Classification Search
USPC ................ 424/405; 514/229.2, 531, 403
See application file for complete search history.

(56) References Cited

U.S. PATENT DOCUMENTS

| 4,329,474 A | * | 5/1982 | Dergazarian | 546/345 |
| 5,232,940 A | | 8/1993 | Hatton et al. | |
| 5,462,938 A | | 10/1995 | Annus et al. | |
| 5,527,973 A | | 6/1996 | Kelsey | |
| 6,096,329 A | | 8/2000 | Jeannin | |
| 6,395,765 B1 | | 5/2002 | Etchegaray | |
| 6,451,339 B2 | * | 9/2002 | Patel et al. | 424/451 |
| 6,716,442 B2 | | 4/2004 | Hunter et al. | |

FOREIGN PATENT DOCUMENTS

| FR | 2851882 A | 9/2004 |
| WO | WO92/11249 A1 | 7/1992 |
| WO | WO95/29171 A1 | 11/1995 |
| WO | WO98/05656 A1 | 2/1998 |
| WO | WO99/63825 A1 | 12/1999 |
| WO | WO01/19189 A1 | 3/2001 |
| WO | WO02/056691 A1 | 7/2002 |
| WO | WO2005/053393 A2 | 6/2005 |

OTHER PUBLICATIONS

Wing et al., "Bioactivation and mode of action of the oxadiazine indoxacarb in insects", Crop Protection, 19, pp. 537-545 (2000).*
Zhao et al., "Block of Two Subtypes of Sodium Channels in Cockroach Neurons by Indoxacarb Insecticides", NeuroToxicology, 26, pp. 455-465 (2005).*
Flouride Action Network Pesticide Project, Indoxacarb, CAS No. 173584-44-6, US Federal Register, accessed Jan. 29, 2010.
Mixtures of arthopodicides and fungicides; Research Disclosure Journal, ISSN 0374-4353; RD 397086 May 1997.
Lapied, et al; Indoxocarb, an oxadiazine insecticide, blocks insect neuronal sodium channels; British Journal of Pharmacology (2001) 132, 587-595.
International Search Report for application No. PCT/US2007/019096 dated Feb. 1, 2008.

* cited by examiner

*Primary Examiner* — Daniel Sullivan
*Assistant Examiner* — Barbara Frazier

(57) ABSTRACT

The present invention provides formulations and methods useful in the control of ectoparasites on a domestic animal, using a formulation comprising Indoxacarb and a veterinarily acceptable carrier that is applied topically to 10% or less of the total surface area of a domestic animal. Other embodiments include these formulations also including one or more additional pesticides such as fipronil.

10 Claims, No Drawings

LOCAL TOPICAL ADMINISTRATION FORMULATIONS CONTAINING INDOXACARB

CROSS-REFERENCE TO RELATED APPLICATIONS

This application is a U.S. 371 filing of International Application Number PCT/US2007/019096 filed Aug. 30, 2007, which claims priority to U.S. provisional application No. 60/841,846, filed Sep. 1, 2006.

BACKGROUND OF THE INVENTION

Animals are often susceptible to infestations by ectoparasites (e.g. flies and lice), and infections by endoparasites (e.g. filariae and intestinal roundworms). Domesticated animals, such as cats and dogs, are often infested with one or more of the following ectoparasites: cat and dog fleas (*Ctenocephalides felis*, *Ctenocephalides canis*, and the like), ticks (*Rhipicephalus* spp., *Ixodes* spp., *Dermacentor* spp., *Amblyoma* spp. and the like), and mites (*Demodex* spp., *Sarcoptes scabei*, *Otodectes cynotis*. and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), including humans.

Similarly, ticks are also harmful to the physical and psychological health of the animal or human. However, the most serious problem associated with ticks is that they are the vector of pathogenic agents, agents which cause diseases in both humans and animal. Major diseases which are caused by ticks include borrelioses (Lyme disease caused by *Borrelia burgdorferi*), babesioses (or piroplasmoses caused by *Babesia* sp.) and rickettsioses (also known as Rocky Mountain spotted fever). Ticks also release toxins which cause inflammation or paralysis in the host. Occasionally, these toxins are fatal to the host. Moreover, mites are particularly difficult to combat since there are very few active substances which act on these parasites and they require frequent treatment.

Likewise, farm animals are also susceptible to parasite infestations. For example, cattle are affected by a large number of parasites. A parasite which is very prevalent among farm animals is the tick genus *Boophilus*, especially *B. microplus* (cattle tick), *B. decoloratus* and *B. anulatus*. Ticks, such as *Boophilus microplus*, are particularly difficult to control because they live in the pasture where the farm animals graze. Other important parasites of cattle include the myiases-producing flies such as *Dermatobia hominis* (known as Berne in Brazil) and *Cochlyomia hominivorax* (screwworm) whose larvae infest the tissue of the host animal. Additionally, the species *Lucilia sericata* (greenbottles), *Lucilia cuprina* (damage caused by this fly is commonly known as blowfly strike in Australia, New Zealand and South Africa) are important causes of myiases in sheep. Insects whose adult stage constitutes the parasite include: *Haematobia irritans* (horn fly); lice such as *Linognathus vituli*, etc.; and mites such as *Sarcoptes scabiei* and *Psoroptes ovis*. The above list is not exhaustive and other ectoparasites are well known in the art to be harmful to animals and humans. These include, for example migrating dipterous larvae such as *Hypoderma* spp. and *Oestrus ovis*.

Control of ectoparasites on domestic animals have been attempted using flea collars containing various insecticides. The ectoparasites, however, remain present in the general vicinity of the animal, such as within the house of a pet owner. The eradication of ectoparasites within the animal environment is difficult unless the environment is permanently covered in an insecticidal substance, in which case toxicity and reinfestation are problematic. Thus, there is a need in the art for persistent and effective agents for eradication of ectoparasites on a domestic animal in order to reduce the periodicity and the cost of anti-ectoparasite agents, wherein such agents must be convenient to store and apply, and present insignificant risk of toxicity to such domestic animal and its environment.

U.S. Pat. No. 5,462,938 discloses novel arthropodicidal compositions and methods relating to oxadiazinyl carboxanilides compounds having efficacy against household, foliar and soil-inhabiting agronomic and non-agronomic pests. A compound disclosed therein, (S)-methyl 7-chloro-2,5-dihydro-2-[[methoxycarbonyl] [4 (trifluoromethoxy)phenyl] amino]carbonyl]indeno[1,2-e][1,3,4]oxadiazine-4a(3H)-carboxylate; common name: Indoxacarb, or DPX-KN128 has been registered by the EPA as a "reduced-risk" pesticide, Chemical Code 067710, CAS No. 173584-44-6, U.S. EPA PC 067710 (S-isomer). *British Journal of Pharmacology* (2001) 132, 587-595; doi:10.1038/sj.bjp.0703853 entitled "*Indoxacarb, an Oxadinzine Insecticide, Blocks Insect Neuronal Sodium Channels*", discloses a study investigating the mode of action of Indoxacarb as an neuronal sodium channel inhibitor in *Periplaneta Americana*. *Research Disclosure*, May 1997, Number 39786 entitled "*Mixtures of Arthropodicides and Fungicides*" discloses the use of Indoxacarb in combination with other arthropodicides in land or aerially applied pesticide formulations for the protection of plants against arthropodal pests. U.S. Pat. No. 6,395,765 B1 relates to compositions for the treatment and protection of parasitic pests on domestic animals that utilize topical application to a localized region of the domestic animal's body.

BRIEF SUMMARY OF THE INVENTION

In one aspect, the present invention provides a composition and method for control of ectoparasites on a domestic animal, including eradication of ectoparasites on a domestic animal, decreasing the number of ectoparasites on a domestic animal, and/or preventing ectoparasite infestation on a domestic animal. The method includes topically applying to a localized region or regions having a cumulative surface area of less than or equal to 10% of the total surface area of the domestic animal an ectoparasitically effective amount of a topical formulation comprising Indoxacarb and veterinarily acceptable carrier. The present composition can also optionally include an additional pesticide.

In a preferred aspect, the present invention provides a composition and method for control of ectoparasite infestation in a domestic animal comprising applying to a localized region or regions having a surface area of less than or equal to 10% of the total surface area of the domestic animal an ectoparasitically effective amount of a local topical formulation comprising Indoxacarb in a veterinarily acceptable solvent and optionally further comprising a crystallization inhibitor.

Preferred solvents, crystallization inhibitors, modes of application and dosages in such formulations are disclosed.

DETAILED DESCRIPTION OF THE INVENTION

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Applicant has found that it is possible to effectively control ectoparasite infestation of domestic animals using a specific type of Indoxacarb formulation: a topical formulation applied to a localized region or regions having a surface area of less than or equal to 10% of the total surface area of the domestic animal. The formulations and methods are especially advantageous for animals in situations where it is difficult or time-consuming to treat all the animals orally or via injection. Thus, the present invention provides topical formulations useful in control of ectoparasites comprising Indoxacarb and a veterinarily acceptable solvent. It has been found by Applicant that certain Indoxacarb local topical formulations are surprisingly effective and persistent.

Definitions

The following definitions relating to Applicant's disclosure are provided.

The term "control of ectoparasites on a domestic animal" as used herein includes eradication of ectoparasites on a domestic animal, decreasing the number of ectoparasites on a domestic animal, and/or preventing ectoparasite infestation on a domestic animal.

As used herein, the term "domestic animal" includes any animal that is kept by humans as a companion animal, pet, working animal or as livestock for food, fur, leather, wool or other animal product; or an animal that is found in association with humans such that control of ectoparasites on such animal is desirable. Common domestic animals in which the present invention will be particularly useful include a cow, horse, ass, pig, camel, bird, dog, cat, deer, sheep, or goat.

As used herein, the term "ectoparasites" includes parasites, in any stage of life including eggs, larvae or adult form, that live on the outside of an animal's body. Common ectoparasites that are problematic on domestic animals include, for example, fleas, lice, ticks and mites.

Arthropod ectoparasites of mammals and birds are often of particular concern. Exemplary athropods include those summarized in Table A, as follows.

TABLE A

Summary Of Taxonomy for Important Arthropod Pests

| Subphylum | Class | Order | Examples |
|---|---|---|---|
| Trilobita | | | |
| Cheliceratac helicera and pedipalps | | | |
| | Merostomata | | |
| | Arachnida | | |
| | | Araneae | spiders |
| | | Scorpionida | scorpions |
| | | Acari | mites and ticks |
| Uniramia | Chilopoda | | centipedes |
| | Diplopoda | | millipedes |
| | Pauropoda | | Soft bodied myriapods |
| | Insecta | Hymenoptera | bees, wasps |
| | | Lepidoptera | moths, butterflies |
| | | Hoptera | grasshoppers |

TABLE A-continued

Summary Of Taxonomy for Important Arthropod Pests

| Subphylum | Class | Order | Examples |
|---|---|---|---|
| | | Diptera | true flies |
| | | Hemiptera | true bugs |
| | | Coleoptera | beetles |

Thus, insect pests include, e.g., biting insects, such as flies and mosquitoes, mites, ticks, lice, fleas, true bugs, parasitic maggots, and the like.

Biting insects include, e.g., migrating *diperous* larvae as *Hypoderma* sp. in cattle, *Gastrophilus* in horses, and *Cuterebra* sp. in rodents, as well as biting flies and mosquitoes of all types. For example, bloodsucking adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, the tsetse fly or *Iossina* spp. Parasitic fly maggots include, e.g., the bot fly (*Oestrus ovis* and *Cuterebra* spp.], the blow fly or *Phaenicia* spp., the screwworm or *Cochliomyia hominivorax*, the cattle grub or *Hypoderma* spp., and the fleeceworm. Mosquitoes, include, for example, *Culex* spp., *Anopheles* spp., and *Aedes* spp.

Mites include *Mesostigmata* spp., e.g., mesostigmatids such as the chicken mite, *Dermanyssus gallinae*; itch or scab mites such as *Sarcoptidae* spp., for example, *Sarcoptes scabiei*; mange mites such as *Psoroptidae* spp., including *Chorioptes bovis* and *Psoroptes ovis*; chiggers, e.g., *Trombiculidae* spp., for example the North American chigger, *Trombicula alfreddugesi*.

Ticks include, e.g., soft-bodied ticks including *Argasidae* spp., for example *Argas* spp. and *Ornithodoros* spp.; hard-bodied ticks including *Ixodidae* spp., for example *Rhipicephalus sanguineus*, and *Boophilus* spp.

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp., such as oriental rat flea (*Xenopsylla cheopis*); and *Pulex* spp., such as human flea (*Pulex initans*).

True bugs include, e.g., *Cimicidae* or e.g., the common bed bug (*Cimex lectularius*); *Triatominae* spp., including *triatomid* bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other arthropod pests and ectoparasites are known to the art, and are also contemplated to be treated by the compounds of the invention. These are enumerated in great detail in *Medical And Veterinary Entomology*, by D. S. Kettle, Publ. John Wiley & Sons, New York and Toronto; *Control Of Arthropod Pests Of Livestock: A Review Of Technology*, by R. O. Drummand, J. E. George, and S. E. Kunz, Publ. CRC Press, Boca Raton, Fla., the contents of both of which are incorporated by reference herein in their entireties.

As used herein an "ectoparasitically effective amount" is an amount effective to eradicate ectoparasites on a domestic animal, decrease the number of ectoparasites on a domestic animal, and/or prevent ectoparasite infestation on such animal.

As used herein the term "Indoxacarb" or DPX-KN128 or the designation KN128 refers to the S isomer of Formula I

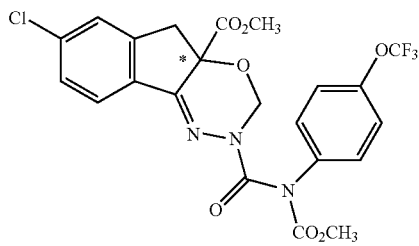

wherein * represents an optically active center.

The systematic chemical name for Indoxacarb is (S)-methyl 7-chloro-2,5-dihydro-2-[[methoxycarbonyl)[4-(trifluoromethoxy)phenyl]amino]carbonyl]indeno[1,2-e][1,3,4]oxadiazine-4a(3H)-carboxylate. The R isomer of Formula I or (R)-methyl 7-chloro-2,5-dihydro-2-[[methoxycarbonyl)[4-(trifluoromethoxy)phenyl]amino]carbonyl ]indeno[1,2-e][1,3,4]oxadiazine-4a(3H)-carboxylate does not display insecticidal activity. WO/9963825 describes the use of various mixtures of the active S isomer and the inactive R isomer as well as the substantially pure S isomer. The S isomer has been designated as DPX-KN128 and the R isomer as DPX-KN127 by DuPont and that nomenclature will used for the sake of convenience in this specification. Indoxacarb, or DPX-KN128 has been registered as CAS No. 173584-44-6, The compounds of Formula I can be prepared by one or more of the methods disclosed in WO 92/11249, WO 95/29171 and WO 98/05656 as shown in Scheme 1.

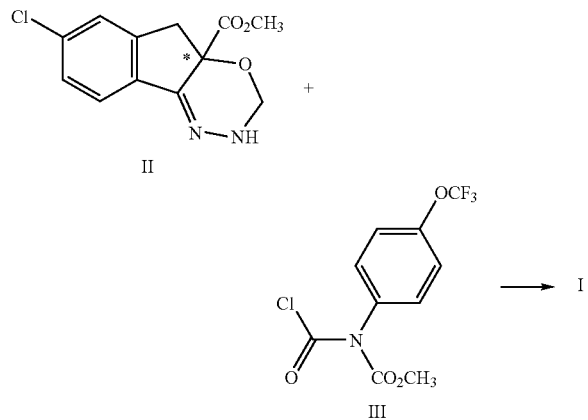

As used herein, a "local topical formulation" is a fluid formulation applied externally to less than or equal to 10% of the total surface area of an animal. The "local topical formulation" may be referred to herein as "the formulation of the present invention." The local, topical formulation will be a fluid (including aqueous suspensions) such as pour-on formulations and spot-on formulations, spray-on formulations, emulsions, oils, creams, and ointments. As used herein, a "local topical administration formulation" is a fluid formulation including an amount of Indoxacarb and a veterinarily acceptable carrier that is effective in eradicating ectoparasites on a domestic animal, decreasing the number of ectoparasites on a domestic animal, and/or preventing ectoparasite infestation on a domestic animal when applied to less than or equal to 10% of the total surface area of a domestic animal. The "local topical formulation" may be referred to herein as "the formulation of the present invention." In some preferred embodiments, the local topical formulation may include a crystallization inhibitor. A "fluid formulation" includes, for example, liquid formulations such as pour-on formulations, spot-on formulations and spray-on formulations which maybe in the form of solutions, emulsions (oil-in-water or water-in-oil), suspoemulsions, microemulsions, suspensions (aqueous or non-aqueous), oils, creams and ointments. A "fluid formulation" may also include dusts, water dispersible granules, wettable powders and aerosols. The "fluid formulation" may be ready-to-use or require preparation such as dilution with water prior to use.

As used herein the term "persistent efficacy," means that a formulation of the present invention maintains the ability to control ectoparasites (i.e., eradicate ectoparasites on a domestic animal, decrease the number of ectoparasites on a domestic animal, and/or prevent ectoparasite infestation on a domestic animal) over a specified period of time or conditions; for example, throughout a given number of aqueous washes, or over a given number of days, weeks or months. In some embodiments, efficacy is sufficiently persistent such that no more than a 20%, 10%, or 5% decrease in efficacy is seen after a single treatment. In this context the term "efficacy" refers to the ability of a formulation to control ectoparasite infestation.

As used herein, the terms "spot-on" and "pour-on" refer to formulations applied to a localized region or regions on an animal having a cumulative surface area of less than or equal to 10% of the total surface area of the animal, and also to the method of applying a composition to a localized surface area of an animal wherein said localized area or areas cumulatively comprise less than or equal to 10% of the total surface area of the animal.

As used herein, the term "veterinarily acceptable" refers to ingredients, compositions or methods of treatment that do not cause significant adverse reactions in or on a domestic animal, and additionally do not pose a danger of human toxicity or other adverse reactions in the surrounding environment of such animal in situations where humans may be exposed to such environment.

The term "veterinarily acceptable carrier," as used herein, refers to all of the ingredients within a composition of the invention except Indoxacarb, or in the case of a composition containing Indoxacarb plus one or more additional pesticidally active ingredients, the ingredients in such composition except the Indoxacarb and the other pesticidally active ingredients. Examples of ingredients or compounds that may be comprised within the veterinarily acceptable carrier include solvents, crystallization inhibitors, antioxidants, adjuvants, cosolvents, colorants, surfactants, oils, light stabilizers, tackifiers, suspending agents, propellants, bulking agents and fragrance enhancers or maskers.

As used herein, the words "comprises" or "comprising" are intended as open-ended transition phrases meaning the inclusion of the named elements, but not necessarily excluding other unnamed elements.

As used herein, the phrases "consists essentially of" and "consisting essentially of" are intended to mean the exclusion of additional components and/or agents that have a material effect on the basic properties of the formulations of the invention. In particular, an additional component and/or agent that inhibits the crystallization of Indoxacarb and/or a pesticide agent in a formulation would have a material effect on the formulation. Therefore, such a crystallization inhibitor would not be included when the terms "consists essentially of" and "consisting essentially of" are employed, unless that crystallization inhibitor was explicitly included in that formulation.

The phrases "consisting of" or "consists of" are intended as a transition meaning the exclusion of all but the recited elements with the exception of only minor traces of impurities.

Methods and Formulations Targeting Ectoparasites on Domestic Animals

In one aspect, the present invention provides a method for controlling ectoparasite infestation on a domestic animal (e.g. elimination and/or prevention of infestations of ectoparasites such as adult fleas or ticks.) The method includes topically applying to a localized region of skin on the animal, having a surface area of less than or equal to 10% of the total surface area of the domestic animal, an ectoparasitically effective amount of a local topical formulation comprising Indoxacarb and a veterinarily acceptable carrier.

The formulations of the present invention include so called "pour-on" and "spot-on" formulations. In addition to application of the formulations of the invention onto the surface of healthy or normal regions of the skin of domestic animals, such localized regions may also include, or may be wholly comprised of, a wound to the dermal layer, such as a cut or sore. Thus, in some embodiments, the present invention is also useful in treating ectoparasite infection of a wound.

In some embodiments, the formulation is applied to a single localized region that is equal to or less than 10%, 5% or 2% of the total surface area of the animal, or is applied to a combination of two or more localized regions or areas of the skin of a domestic animal that together comprise less than 10%, 5% or 2% of the total surface area of the animal. Without being limited by any particular mechanism of action, it is believed that the active ingredient, Indoxacarb diffuses after localized topical application beyond the localized region to provide ectoparasitic control over the entire, or a significant portion of the domestic animal's body. In preferred embodiments, the formulations of the present invention are applied onto a single spot or region of the skin using "spot-on" or "pour-on" applications to the skin of the animal. In some embodiments especially useful for cats and dogs, this application is localized over a surface area equal to or less than 10 cm$^2$, especially between 5 and 10 cm$^2$. In some particularly preferred embodiments, the formulation is applied at one or more points along the backline of the animal. For example, for low dose volumes a single spot between the shoulders will be suitable; however for high dose volumes multiple locations along the back is recommended.

In some preferred embodiments, the formulations are particularly advantageous due to their efficacy, persistency, and the pleasant appearance of the animal's fur after application and drying, in that such preferred formulations have been designed to minimize or eliminate crystallization on the hairs and maintain the cosmetic appearance of the coat without stickiness or a sticky appearance, even when high concentrations of active material are present. Thus, in another aspect, the present invention provides a local topical formulation for eradication, reduction and/or prevention of ectoparasite infestation in a domestic animal comprising an effective amount of Indoxacarb and a veterinarily acceptable carrier comprising a crystallization inhibitor. A crystallization inhibitor as used herein is a substance that minimizes formation of visible Indoxacarb crystals or precipitates of Indoxacarb and/or any other pesticide agent from the formulation after application to the animal. Candidate compounds for use as crystallization inhibitors may be tested using assays commonly known in the art. For example, the candidate crystallization compound(s) may be added to Indoxacarb and a veterinarily acceptable solvent on a glass slide at 20° C. for 24 hours, after which the composition is observed with the naked eye to determine whether crystals are formed. Alternatively, a local topical formulation including a candidate compound may be applied to a domestic animal at room temperature, after which the animal is observed with the naked eye to determine whether crystals are formed.

Examples of other crystallization inhibitors include: triacetin, polyvinylpyrrolidone, polyvinyl alcohols, copolymers of vinyl acetate and vinylpyrrolidone, polyethylene glycols, polyethoxylated sorbitan esters; lecithin, acrylic derivatives such as methacrylates and others, anionic surfactants such as alkali metal stearates, especially of sodium, of potassium or of ammonium; calcium stearate; triethanolamine stearate; sodium abietate; alkylsulphates, especially sodium laurylsulphate and sodium cetylsulphate; sodium dodecylbenzenesulphonate, sodium dioctylsulphosuccinate; fatty acids, especially those derived from copra oil, cationic surfactants such as water-soluble quaternary ammonium salts of formula N+R'R"R'"R"", Y– in which the R radicals are optionally hydroxylated hydrocarbon radicals, and Y– is an anion of a strong acid, such as halide, sulphate and sulphonate anions; cetyltrimethylammonium bromide is among the cationic surfactants utilizable, the amine salts of formula N+R'R"R'" in which the R radicals are optionally hydroxylated hydrocarbon radicals; octadecylamine hydrochloride is among the cationic surfactants utilizable, the non-ionic surfactants such as optionally polyethoxylated sorbitan esters, in particular Polysorbate 80, polyethoxylated alkyl ethers; polyethylene glycol stearate, polyethoxylated castor oil derivatives, polyglycerol esters, polyethoxylated fatty alcohols, polyethoxylated fatty acids, copolymers of ethylene oxide and propylene oxide, amphoteric surfactants such as substituted lauryl betaine compounds, or preferably a mixture of at least two of these.

The crystallization inhibitor may be present in any appropriate proportion and concentration so as to be effective in inhibiting crystallization of the particular dosage of Indoxacarb within the selected formulation. A combination of crystallization inhibitors may also be used. In some embodiments, the proportion of crystallization inhibitor(s) is present from 1 to 60% (W/V), from 5 to 50% (W/V), or from 10 to 40% (W/V). Thus, in the most preferred embodiments, once deposited, the formulation diffuses over the animal's body and then dries without crystallizing or modifying the appearance (in particular absence of any whitish deposit or dusty appearance) or the feel of the fur or skin of the animal.

Preferred formulations are sufficiently persistent in terms of efficacy so as to reduce the periodicity and the cost associated with administration of the formulation to the domestic animal. In some cases, the formulation is applied no more than twice per week, no more than once per week, no more than once per month, or no more than once every three months. Thus, certain formulations of the present invention maintain persistent efficacy for at least 48 hours, 1 week, 1 month, 2 months or in some cases up to 3 months. The formulations may also be sufficiently persistent to withstand washing of the domestic animal with an aqueous solution (e.g. soap and water.) Thus, the formulation may maintain persistent efficacy after at least one or even five aqueous solution washes.

A variety of ectoparasites may be targeted using the formulations of the present invention. In some embodiments, the ectoparasite is a flea, fly, or louse, including flea eggs, flea larvae, fly eggs or fly larvae. Where the formulations of the present invention are designed to target flea eggs, flea larvae, fly eggs or fly larvae, the life-cycle of the flea and/or fly is broken thereby reducing environmental population pressures. For the purposes of the present invention, the term flea is understood to refer to all the usual or accidental species of parasitic flea of the order *Siphonaptera*, and in particular the genus *Ctenocephalides*, in particular the cat flea (*C. felis*) and dog flea (*C. canis*), rat flea (*Xenopsylla cheopis*) and human flea (*Pulex irritans*).

Any appropriate domestic animal may be treated with the formulations of the present invention in situations where it is desirable to control ectoparasites on such animal, or in the environs of such animal. In certain preferred embodiments, the domestic animal is a mammal such as a cow, horse, ass, pig, bird, camel, dog, cat, deer, sheep, or goat.

The local topical formulations may be prepared by simply mixing the constituents as defined above, or in cases where the carrier is an emulsion, suspension or suspoemulsion, aggressive mixing or homogenization will be required and in the cases where the Indoxacarb (DPX-KN128) is present in solid form (suspensions, susopemusions, dusts, powders and granules) milling will be required to reduce the Indoxacarb (DPX-KN128) particle size. Methods of preparations of the formulations of the invention will be obvious to one skilled in this art due to the chemically-defined nature of Indoxacarb and the preferred ingredients in the claimed formulations. For example, the active material may be mixed in the veterinarily acceptable solvent and other components of the veterinarily acceptable carrier are then added, or the veterinarily acceptable carrier may be constituted to comprise all of the ingredients of the formulation except Indoxacarb, and then the Indoxacarb (and optionally other pesticidally active ingredients) are then added to the veterinarily acceptable carrier composition.

In some embodiments, an additional component within the carrier will be an antioxidant. Useful antioxidants include, for example, butylhydroxyanisole, butylhydroxytoluene, ascorbic acid, sulphites, metabisulphites, or thiosulphates (e.g. sodium thiosulphate, sodium metabisulphite, potassium metabisulphite, etc.), propyl gallate, and/or tocopherol, or a mixture of not more than two of these agents.

One or more additional pesticidal agents may be included within the formulations of the invention. Useful pesticides include insect growth regulators, organophosphate pesticides, carbamate pesticides, organochlorine pesticides, pyrethrin pesticides, pyrethroid pesticides, nicotine pesticides, neonicotinoid pesticides, copper-containing pesticides, anthelmintic agents, benzimidazole pesticides, salicylanilide pesticides, substituted phenol pesticides, pyrimidine pesticides, and imidazothiazole pesticides. Particularly preferred are formamidine insecticides such as amitraz, semicarbazone insecticides such as metaflumazone and phenylpyrazoles such as fipronil. Fipronil has been described in U.S. Pat. Nos. 5,232,940, 6,096,329, 6,395,765 and 6,716,442, the contents of which are incorporated herein by reference. In one such embodiment the formulation includes an effective amount of fipronil and Indoxacarb.

In some embodiments, the imidazothiazole pesticide is levamisole. The pyrimidine pesticide may be pyrantel. The substituted phenol pesticide may be nitroxynil. The salicylanilide pesticide may be closantel or oxyclozanide. The benzimidazole pesticide may be albendazole or triclabendazole. The anthelmintic agent may be a macrocyclic lactone such as an avermectin (e.g., ivermectin) or a milbemycin (e.g., moxidectin). The organophosphate pesticide may be dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion, phosalone, naphthalophos or pyraclofos. The carbamate pesticide may be carbaryl, carbofuran, aldicarb, or carbofuran. The pyrethroid pesticide may be allethrin, resmethrin, permethrin, deltamethrin or tralomethrin. The copper-containing pesticide may be copper (II) hydroxide, or copper oxychloride sulfate (i.e. (Cu2Cl(OH)3) mixed with (Cu4(OH) 6(SO4)). The neonicotinoid pesticide may be imidacloprid, nitenpyram or dinotefuran.

Additionally, in some embodiments, the pesticide agent is a pyrethrin pesticide, *Bacillus thuringensis* toxin, chlorobenzilate, cyfluthrin, cypermethrin, dicofol, endosulfan, esfenvalerate, fenvalerate, lambda-cyhalothrin, methoxychlor, sulfur, cyclodiene, ryania, KT-199 (an antihelminthic antibiotic), or praziquantel.

The insect growth regulator may be a chitin synthesis inhibitor or a juvenile growth hormone mimic. In certain embodiments, the insect growth regulator is azadirachtin, diofenolan, fenoxycarb, hydroprene, kinoprene, methoprene, pyriproxyfen, tetrahydroazadirachtin, chlorfluazuron, cyromazine, diflubenzuron, fluazuron, flucycloxuron, flufenoxuron, hexaflumuron, lufenuron, novaluron, tebufenozide, teflubenzuron, and triflumuron.

These additional pesticidal agents may be present in amounts to optimize and efficacy and persistency of the formulation. Particularly. These additional pesticidal agents may be present from about 0.05% to about 80%. In a preferred embodiment, the additional pesticidal agent in the formation is permethrin, present an amount from about 30% to about 75%. In another preferred embodiment, the additional pesticidal agent is fipronil, present in an amount from about 5% to about 25%.

In another preferred embodiment, the additional pesticidal agent is ivermectin, present in an amount from about 0.05% to about 10%. In another preferred embodiment, the additional pesticidal agent is abamectin, present in an amount from about 0.05% to about 10%. In another preferred embodiment, the additional pesticidal agent is moxidectin, present in an amount from about 0.05% to about 10%. In another preferred embodiment, the additional pesticidal agent is doramectin, present in an amount from about 0.05% to about 10%. In another preferred embodiment, the additional pesticidal agent is eprinomectin, present in an amount from about 0.05% to about 10%. In another preferred embodiment, the additional pesticidal agent is selamectin, present in an amount from about 0.05% to about 10%. In another preferred embodiment, the additional pesticidal agent is methoprene, present in an amount from about 1% to about 20%. In another preferred embodiment, the additional pesticidal agent is S-methoprene, present in an amount from about 1% to about 20%.

Although the selection of an appropriate solvent for the Indoxacarb will be important aspect in preparation of an effective, persistent and cosmetically-desirable formulation, a variety of veterinarily acceptable solvents are useful in the present invention. A "veterinarily acceptable solvent," as used herein, is a solvent that is non-toxic when topically applied to a domestic animal and is capable of sufficiently solvating indoxacarb to form a solution. For example, veterinarily acceptable solvents of the present invention do not cause rashes or inflammation of the dermal layer on a domestic animal. The veterinarily acceptable solvent is typically not easily ignited, or if ignited, does not burn rapidly. The veterinarily acceptable solvent may also appear non-greasy after applying to said domestic animal.

In some embodiments the veterinarily acceptable solvent has a dielectric constant of between 0 and 40, between 0 and 20, or between 0 and 10.

Examples of veterinarily acceptable solvents are useful in the present invention, including diethylene glycol monobutyl ether, glycerin triacetate, diethylene glycol monomethyl ether, diethylene glycol monoethyl ether, benzyl benzoate, ethylene glycol monobutyl ether, ethyl lactate, dipropylene glycol monomethyl ether, ethylene glycol monobutyl ether acetate, isopropyl alcohol, benzyl alcohol, ethyl acetoacetate, 2-pyrrolidinone, dimethyl isosorbide, diacetone alcohol, tetrahydrofurfuryl alcohol, propylene glycol monomethyl ether, ethanol, propylene carbonate, diethyl phthalate, glycerine triacetate heptyl acetate, methyl caprylate/caprate, N,N-dimethyl caprylamide, pentyl acetate, hexyl acetate, cyclohexyl acetate, ethylene glycol diacetate, methoxypropyl acetate, furfuryl alcohol, dibutyl phthalate, N-methylpyrrolidinone, glycerol formal, 2,6-dimethyl-4-heptanone, methyl ethyl ketone, methyl isobutyl ketone and cyclohexanone.

In some preferred embodiments, the veterinarily acceptable solvent for Indoxacarb is a glycol ether or alkyl acetate, such as ethyl acetoacetate. In certain especially preferred embodiments the veterinarily acceptable solvent is ethyl acetoacetate or dipropylene glycol monomethyl ether.

Some of the formulations of the present invention may also include additional agents such as adjuvants, co-solvents, colorants, surfactants, spreading oils, antioxidants, light stabilizers, suspending agents, propellants, bulking agents and/or tackifiers. Colorants are all colorants which are licensed for use on animals and which can be dissolved or suspended. The selection and use of such additional agents to achieve certain desirable characteristics in topical formulations are well known in this art.

Examples of light stabilizers are substances from the benzophenone class, or novantisolic acid.

Examples of tackifiers are cellulose derivatives, starch derivatives, polyacrylates, polyvinyl pyrrolidone, and natural polymers such as alginates and gelatin.

Adjuvants may include spreading oils such as isopropyl myristate, dipropylene glycol pelargonate, silicone oils, fatty acid esters, triglycerides and fatty alcohols. For example, pour-on and spot-on formulations may advantageously comprise carriers that assist rapid distribution over the surface of the skin and in the coat of the host animal and are generally termed spreading oils. Many spreading oil/solvent combinations are suitable, e.g., oily solutions; alcoholic and isopropanolic solutions, e.g., solutions of 2-octyl dodecanol or oleyl alcohol; solutions in esters of monocarboxylic acids, such as isopropyl myristate, isopropyl palmitate, lauric acid oxalic ester, oleic acid oleyl ester, oleic acid decyl ester, hexyl laurate, oleyl oleate, decyl oleate, caproic acid esters of saturated fatty alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or solutions of esters of aliphatic acids, e.g., glycols. It may be advantageous for a dispersant known from the pharmaceutical or cosmetic industry also to be present. Examples are pyrrolidin-2-one, N-alkylpyrrolidin-2-one, acetone, polyethylene glycol and its ethers and esters, propylene glycol or synthetic triglycerides.

The formulations of the present invention may further include sorbitan monolaurate, dipropylene glycol monomethyl ether, triethanolamine, benzyl alcohol, isopropyl alcohol, and/or ethyl acetoacetate.

Useful anionic surfactants include alkaline stearates, in particular sodium, potassium or ammonium stearate; calcium stearate; triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil.

Useful cationic surfactants include water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used.

Useful cationionic surfactant include amine salts of formula $N^+R'R''R'''$ in which the radicals R are H or optionally hydroxylated hydrocarbon radicals; octadecylamine hydrochloride is among the cationic surfactants which can be used.

Useful nonionic surfactants include polyoxyethylenated sorbitan esters, in particular polysorbate 80, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide. Useful amphoteric surfactants include substituted lauryl compounds of betaine.

The dose and concentration of Indoxacarb in the formulations of the present invention are chosen to optimize the efficacy and persistency of the formulations. In some embodiments, the concentration of Indoxacarb in the formulation is at least 100 g/L, 150 g/L, or 200 g/L; or from 1 to 50% (w/v), 5 to 35% (w/v), or 10 to 20% (w/v). In some preferred embodiments, the concentration is about 200 g/L or 20% (w/v). In certain applications (e.g. where the domestic animal is a pet), the concentration is also chosen to minimize any undesired appearance (e.g. white crystals of Indoxacarb) of the animal after application of the formulation. The total amount of Indoxacarb administered to the domestic animal is typically from 1 to 50 mg per kg of body weight, 2 to 25 mg per kg of body weight, or 5 to 15 mg per kg of body weight.

In some embodiments, the formulation is applied to the animal's back and at several points or along the line of the back, and applied in low volume, such as 5 to 20 ml per 100 kg, or 10 ml per 100 kg. In some embodiments, the total volume is 10 to 150 ml per animal, sometimes limited to 50 ml. For example, the volume applied to cats may be from about 0.3 to 1 ml for cats, and from about 0.5 to 5 ml for dogs, according to the weight of the animal.

In some embodiments, the veterinarily acceptable carrier may be in the form of an emulsion or solution for application to a localized region of the animal's skin (e.g. between the two shoulders as in spot-on type applications). Formulations may include solutions to be sprayed, poured, spread, or spotted onto the animal, oils, creams, ointments or any other appropriate fluid formulation for topical administration. Pour-on and spot-on formulations may be poured, spotted or sprayed onto limited areas of the skin. Pour-on and spot-on formulations may be prepared by dissolving, suspending or emulsifying the active compound in suitable solvents or solvent mixtures which are tolerated by the skin. The formulation maybe in the form of a stable-at-room-temperature, ready-to-use solution that is applied topically and locally on the animal.

Veterinarily acceptable emulsions are either of the water-in-oil type or of the oil-in-water type. They are prepared by dissolving the Indoxacarb either in the hydrophobic or in the hydrophilic phase and homogenizing this phase with the solvent of the other phase, with the aid of suitable emulsifiers and, if appropriate, other adjuvants such as colorants, absorption accelerators, preservatives, antioxidants, light stabilizers, and/or viscosity-increasing substances.

Examples of hydrophobic phase (oils) include paraffin oils, silicone oils, natural vegetable oils such as sesame seed oil, almond oil, castor oil, synthetic triglycerides such as caprylic/capric acid biglyceride, triglyceride mixture formed from vegetable fatty acids of chain length C8-12 or with other specifically selected natural fatty acids, partial glyceride mixtures of saturated or unsaturated fatty acids which may also contain hydroxyl groups, and mono- and diglycerides of the C8/C10-fatty acids. Fatty acid esters such as ethyl stearate, di-n-butyryl adipate, hexyl laurate, dipropylene glycol pelargonate, esters of a branched fatty acid of medium chain length with saturated fatty alcohols of chain length C16-C18, isopropyl myristate, isopropyl palmitate, caprylic/capric esters of saturated fatty alcohols of chain length C12-C18, isopropyl stearate, oleyl oleate, decyl oleate, ethyl oleate, ethyl lactate, waxy fatty acid esters such as dibutyl phthalate, diisopropyl adipate, ester mixtures related to the latter, and fatty alcohols such as isotridecyl alcohol, 2-octyldodecanol, cetylstearyl alcohol and oleyl alcohol.

Hydrophilic phase solvents include water, alcohols, propylene glycol, glycerol, sorbitol and their mixtures. Emulsifiers include non-ionic surfactants, for example polyoxyethylated castor oil, polyoxyethylated sorbitan monooleate, sorbitan monostearate, glycerol monostearate, polyoxyethyl stearate, alkylphenol polyglycol ethers; ampholytic surfactants such as di-sodium N-lauryl-β-iminodipropionate or lecithin; anionic surfactants such as sodium lauryl sulphate, fatty alcohol ether sulphates, the monoethanolamine salt of mono/dialkyl polyglycol ether orthophosphoric esters; cationic surfactants such as cetyltrimethylammonium chloride.

Useful viscosity-increasing substances and substances which stabilize the emulsion include carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica, or mixtures of the substances mentioned.

EXAMPLES

The materials and methods of the present invention are further illustrated by the examples which follow. These examples are offered to illustrate, but not to limit, the claimed invention.

Example 1

Dose Response Study on Canines Against Fleas Using Indoxacarb Local Topical Administration Containing Dimethyl Isosorbide and Propylene Glycol Monomethyl Ether A non-blinded prospective longitudinal artificial infestation parasite efficacy pen study was conducted with a fully randomized design (ranking and blocking based on breed and pre-treatment flea count). There were 5 treatment groups of 6 dogs each, and an untreated control group.

Thirty-three (33) adult dogs (Labrador Retrievers and Jack Russell Terriers) were inducted, clinically examined, weighed, identified and allocated to study pens on Day-7. Each dog was artificially infested with 100 fleas (*Ctenocephalides felis*) on Day-5 and again on Day-2. On Day-1 flea thumb counts were performed on all dogs and 30 dogs were selected for inclusion. These dogs were randomly allocated to 5 similar groups of 6 animals on the basis of breed and flea counts, and groups were allocated to study pens. On Day 0, Groups B, C, D and E were treated with a local topical administration formulation containing Indoxacarb (DPX-K128) dissolved in a mixture of Dimethyl Isosorbide (DMI) and Propylene Glycol Monomethyl Ether (90% Dimethyl Isosorbide (DMI) and 10% Propylene Glycol Monomethyl Ether by volume) to form a total concentration of 75, 100, 125 or 150 g/L of Indoxacarb (DPX-K128). The starting material to prepare the formulation was a mixture of DPX-K128- and DPX-KN127 (the R-isomer of Formula 1) and contained 70.43% Indoxacarb (DPX-K128). Hence for every 1 gram of Indoxacarb (DPX-K128) required, 1.42 grams of this mixture was used. The formulation was administered via spot-on application (i.e. applying in liquid form to less than or equal to 10% of the surface area of the animal) to the dorsal midline at the rate of 0.1 mL/1 kg. Group A remained untreated as controls. Group B was dosed at the rate of 7.5 mg/kg; Group C at the rate of 10.0 mg/kg; Group D at the rate of 12.5 mg/kg; and Group E at the rate of 15.0 mg/kg.

Flea thumb counts were performed at 24 hours. Flea comb counts were performed at 48 hours post-treatment and all dogs then treated with Capstar® oral tablets (Nitenpyram, Novartis Animal Health) to remove all fleas prior to the next infestation. Animals were re-infested with 100 adult fleas at 7, 14, 21 and 28 days post-treatment. At 24 hours after each infestation, flea comb counts were performed followed by Capstar treatment.

In the first 48 hours post treatment Group D (12.5 mg/kg) and Group E (15.0 mg/kg) showed 99.0% and 100% reduction of flea infestation at 24 hrs and 100% and 99.4% reduction at 48 hrs respectively. Group B (7.5 mg/kg) and C (10.0 mg/kg) also showed excellent knockdown efficacy, both achieving 97.9% reduction at 24 hrs and 99.4% and 100% respectively at 48 hrs.

All four groups showed excellent persistent efficacy being at or near 100% reduction (all ≧99%) from the 48 hour count until 29 days post-treatment.

Example 2

Effect of Washing on Persistency

At completion of the study described in Experiment 1 above, a further washing study was conducted using the six dogs in Group E for a further two weeks.

During the two-week period, four of the six dogs from Group E were washed twice weekly in a non-insecticidal hydrobath, while the other two dogs from Group E were not washed and acted as controls. On Day 43 post-treatment, the 6 dogs were infested with 100 fleas and then had their ability to retain a flea infestation assessed on Day 44 by a flea comb count. The results are shown in Table 1 below.

TABLE 1

| Dog No. | Group | Flea Count | Group Average Count |
|---|---|---|---|
| 5 | Treated Wash | 4 | 3 |
| 25 | Treated Wash | 5 | |
| 35 | Treated Wash | 1 | |
| 38 | Treated Wash | 2 | |
| 19 | Treated Non-Wash | 0 | 0 |
| 44 | Treated Non-Wash | 0 | |

These results demonstrated that all the dogs had low flea counts and were still resistant to maintaining a flea infestation, suggesting excellent persistence at 44 days even after 4 thorough shampoo hydrobath washes.

Example 3

Efficacy Study on Canines Against Fleas Using 15 mg/kg Indoxacarb Local Topical Administration Formulations The study was a non-blinded, prospective longitudinal randomized clinical efficacy pen study with groups of 3 dogs each receiving one of 5 treatments; 4 test formulation treatments, and a negative control (no treatment). Animals were ranked on the basis of breed and pre-treatment flea count, then randomly allocated to groups from blocks. Animals were artificially infested and parasite counts performed according to standardized methods.

Twenty (20) adult dogs (Labrador Retrievers and Jack Russell Terriers) were inducted into the study on Day-6 and each artificially infested with 100 fleas (*Ctenocephalides felis*) on Day-4. On Day-1, flea counts were performed and 18 dogs selected for inclusion. The dogs were randomly allocated to 6 similar groups of 3 animals on the basis of breed and flea counts, and groups were randomly allocated to study pens. Each dog was again infested with 100 fleas. On Day-1 flea counts were again performed on all dogs. On Day 0, Groups B, C, D and E were treated with one of 4 different 15.0 mg/kg Indoxacarb (DPX-KN128) local topical administration formulations as shown in Table 2 below. A 3:1 mixture of DPX-KN128:DPX-KN127 on silica was the starting material for the formulations. This material contained 56.2% Indoxacarb (DPX-KN128). Hence for every 1 milligram of Indoxacarb (DPX-KN128) required, 1.78 milligrams of this mixture was used. The formulations were applied as a spot-on dose from the base of the neck to the shoulders. The vehicle for Groups B, C and D was Dimethyl Isosorbide (DMI) and the vehicle for Group E contained 40 g/L Polyvinyl Pyrrolidone, 47 g/L Ethoxylated Castor Oil, 33 g/L Ethanol and was diluted to volume with 1-Methyl-2-Pyrrolidinone. Group A remained untreated.

TABLE 2

| Group | Dose Rate and Formulation | Dose Volume (ml/kg) |
|---|---|---|
| A (control) | — | — |
| B | 15.0 mg/kg Indoxacarb | 1.8 mL/15 kg |
| C | 15.0 mg/kg Indoxacarb 6.0 mg/kg (S)-Methoprene | 1.8 mL/15 kg |
| D | 15.0 mg/kg Indoxacarb 6.0 mg/kg (S)-Methoprene 47.9 mg/kg Permethrin | 2.5 mL/15 kg |
| E | 15.0 mg/kg Indoxacarb | 4.0 mL/15 kg |

Flea counts were performed at 24 and 48 hours post treatment. Flea infestations were repeated at 7, 14, 21, 28, 35 and 42 days post treatment and flea counts were performed at 24 and 48 hours following each infestation.

Treatment with all formulations resulted in excellent (at or near 100% reduction) flea control for 44 days post-treatment with the exception of Group B, for which excellent control was observed for 37 days post-treatment. These results are presented in Table 3.

TABLE 3

Group % Reduction in Flea Counts as Compared to Contemporary Control Counts.

| GROUP | 24 Hr | 48 HR | 8 days | 9 days | 15 days | 16 days | 22 days |
|---|---|---|---|---|---|---|---|
| B | 77.4% | 96.2% | 94.3% | 98.0% | 100.0% | 95.7% | 100.0% |
| C | 82.8% | 98.7% | 98.1% | 100.0% | 100.0% | 100.0% | 98.6% |
| D | 98.9% | 100.0% | 100.0% | 100.0% | 100.0% | 100.0% | 99.3% |
| E | 73.1% | 97.4% | 100.0% | 100.0% | 100.0% | 100.0% | 100.0% |

| GROUP | 23 days | 29 days | 30 days | 36 days | 37 days | 43 days | 44 days |
|---|---|---|---|---|---|---|---|
| B | 99.2% | 98.7% | 98.0% | 100.0% | 100.0% | 95.5% | 100.0% |
| C | 100.0% | 100.0% | 100.0% | 99.1% | 100.0% | 99.0% | 100.0% |
| D | 100.0% | 100.0% | 100.0% | 96.6% | 98.9% | 73.3% | 85.4% |
| E | 100.0% | 100.0% | 100.0% | 98.3% | 100.0% | 96.0% | 99.0% |

Example 4

Exemplary Formulations

Table 4 below provides a listing of certain prepared topical administration formulations.

TABLE 4

| Formulation Number | Ingredients | % w/v |
|---|---|---|
| 1 | Indoxacarb | 10 |
|   | Dipropylene glycol monomethyl ether | QS |
| 2 | Indoxacarb | 10 |
|   | Isopropyl myristate | 2.0 |
|   | Span 20 | 2.0 |
|   | Dipropylene glycol monomethyl ether | QS |
| 3 | Indoxacarb | 10 |
|   | Ethylene glycol monobutyl ether acetate | QS |

TABLE 4-continued

| Formulation Number | Ingredients | % w/v |
|---|---|---|
| 4 | Indoxacarb | 10 |
| | Ethyl lactate | 40 |
| | Isopropyl myristate | 5.0 |
| | Triethanolamine | 0.02 |
| | Isopropyl alcohol | QS |
| 5 | Indoxacarb | 10 |
| | Ethyl acetoacetate | 50 |
| | Isopropyl myristate | 5.0 |
| | Triethanolamine | 0.02 |
| | Isopropyl alcohol | QS |
| 6 | Indoxacarb | 20 |
| | Triacetin | 30 |
| | Triethanolamine | 0.02 |
| | Ethyl acetoacetate | QS |
| 7 | Indoxacarb | 20 |
| | Triacetin | 25 |
| | Polysorbate 80 | 10 |
| | Triethanolamine | 0.02 |
| | Ethyl acetoacetate | QS |
| 8 | Indoxacarb | 20 |
| | Isopropyl myristate | 25 |
| | Triethanolamine | 0.02 |
| | Ethyl acetoacetate | QS |
| 9 | Indoxacarb | 20 |
| | Isopropyl myristate | 10 |
| | Propylene carbonate | 35 |
| | Triethanolamine | 0.02 |
| | Ethyl acetoacetate | QS |
| 10 | Indoxacarb | 20 |
| | Isopropyl myristate | 10 |
| | Dipropylene glycol monomethyl ether | 30 |
| | Triethanolamine | 0.02 |
| | Ethyl acetoacetate | QS |
| 11 | Indoxacarb | 20 |
| | Polysorbate 80 | 10 |
| | Polyvinyl pyrrolidone K-17 | 5 |
| | Triethanolamine | 0.02 |
| | Ethyl acetoacetate | QS |
| 12 | Indoxacarb | 20 |
| | Isopropyl myristate | 10 |
| | Benzyl alcohol | 30 |
| | Triethanolamine | 0.02 |
| | Ethyl acetoacetate | QS |
| 13 | Indoxacarb | 20 |
| | Fipronil | 10 |
| | Ethyl acetoacetate | QS |
| 14 | Indoxacarb | 20 |
| | Fipronil | 10 |
| | Dipropylene glycol monomethyl ether | QS |

Example 5

Evaluation of the Safety, Appearance and Run-Off Potential of Topical Solutions Containing Indoxacarb when Applied on Dogs A series of studies were conducted to evaluate the safety, appearance and potential for run-off of various topical solutions of Indoxacarb following application on adult beagle dogs. For all experiments set forth in Table 5, male and female dogs weighing between 10 and 20 kg were randomly assigned to each formulation group. A dose volume of 1.5 mL was applied to each dog, which delivered a minimum dose of 15 mg indoxacarb/kg body weight. At the time of application, hair at the treatment site was parted and the formulations were applied directly to the skin in a single location between the shoulder blades. The application site and hair coat were then observed closely for spread of the solution, signs of residue and wetness, and to determine if any of the solution ran off the animal following treatment (at 5, 15, 30, 60 and 180 minutes and 24 hours). Skin and hair in proximity to the treatment site were examined for any adverse reactions at 24 hours following treatment.

Table 5 provides a listing of the ingredients of the formulations that were tested in sixteen separate experiments. Each formulation was applied to four dogs in each study with the exception of Study Number X07-055-12 (6 dogs/formulation) and Studies X07-055-13 and X07-055-14 (36 dogs/formulation).

All of the formulations were safe and there were no adverse effects on the skin or hair of treated dogs. Formulations V, Z, AB, AC, AE, AF, AG and AH were identified as having preferred characteristics of a commercial spot-on treatment. These preferred characteristics included: lack of drips or run-off upon application, minimal appearance of residue or crystals upon drying and relatively fast drying of the application site. The formulations with the least desirable characteristics (i.e., appearance of drips/run-off, residue and wetness) were Formulations C, E, G, J, Q, and S. The characteristics of the remaining formulations were intermediate.

TABLE 5

| Study No. | Formulation (% w/v) | Formulation ID |
|---|---|---|
| X07-055-1 | 20% KN128, 30% triacetin, 0.02% triethanolamine, ethyl acetoacetate (qs) | A |
| | 20% KN128, 30% triacetin, 0.02% triethanolamine, 1.5% PVP-90, ethyl acetoacetate (qs) | B |
| | 20% KN128, 30% triacetin, 0.02% triethanolamine, 5% Tween-20, ethyl acetoacetate (qs) | C |
| | 20% KN128, 30% triacetin, 0.02% triethanolamine, 5% Ethyl oleate, ethyl acetoacetate (qs) | D |
| X07-055-2 | 20% KN128, 30% triacetin, 0.02% triethanolamine, 2.5% Ethyl oleate, ethyl acetoacetate (qs) | E |
| | 20% KN128, 30% triacetin, 0.02% triethanolamine, 5% Ethyl oleate, ethyl acetoacetate (qs) | C |
| | 20% KN128, 30% triacetin, 0.02% triethanolamine, 10% Ethyl oleate, ethyl acetoacetate (qs) | F |
| X07-055-3 | 20% KN128, 30% triacetin, 0.02% triethanolamine, 5% Miglyol 840, ethyl acetoacetate (qs) | G |
| | 20% KN128, 30% triacetin, 0.02% triethanolamine, 10% Miglyol 840, ethyl acetoacetate (qs) | H |
| | 20% KN128, 30% triacetin, 0.02% triethanolamine, 5% Brij 30, ethyl acetoacetate (qs) | I |
| X07-055-4 | 20% KN128, 20% triacetin, 0.02% triethanolamine, ethyl acetoacetate (qs) | J |
| | 20% KN128, 20% triacetin, 0.02% triethanolamine, 5% PVP K-30, ethyl acetoacetate (qs) | K |
| | 20% KN128, 20% triacetin, 0.02% triethanolamine, 10% Miglyol 840, ethyl acetoacetate (qs) | L |
| X07-055-5 | 20% KN128, 20% triacetin, 0.02% triethanolamine, 10% Miglyol 812, ethyl acetoacetate (qs) | M |
| | 20% KN128, 20% benzyl alcohol, 0.02% triethanolamine, 5% PVP K-30, ethyl acetoacetate (qs) | N |
| | 20% KN128, 20% benzyl alcohol, 0.02% triethanolamine, 10% Miglyol 840, ethyl acetoacetate (qs) | O |
| X07-055-6 | 20% KN128, ethyl lactate (qs) | P |
| | 20% KN128, ethyl acetoacetate (qs) | Q |
| | 20% KN128, triacetin (qs) | R |

TABLE 5-continued

| Study No. | Formulation (% w/v) | Formulation ID |
|---|---|---|
| X07-055-7 | 20% KN128, propylene carbonate (qs) | S |
|  | 20% KN128, dipropylene glycol monomethyl ether (qs) | T |
|  | 20% KN128, benzyl alcohol (qs) | U |
| X07-055-8 | 20% KN128, 25% triacetin, 25% ethyl acetoacetate, isopropyl alcohol (qs) | V |
|  | 20% KN128, 25% triacetin, 25% ethyl acetoacetate, Miglyol 812 (qs) | W |
|  | 20% KN128, 25% triacetin, 25% ethyl acetoacetate, dipropylene glycol monomethyl ether (qs) | X |
| X07-055-9 | 20% KN128, 25% triacetin, dipropylene glycol monomethyl ether (qs) | Y |
|  | 20% KN128, 25% triacetin, ethyl lactate (qs) | Z |
|  | 20% KN128, 47.9% permethrin, ethyl acetoacetate (qs) | AA |
| X07-055-10 | 20% KN128, 25% triacetin, 25% ethyl acetoacetate, isopropyl alcohol (qs) | AB |
|  | 20% KN128, 20% triacetin, 25% ethyl acetoacetate, isopropyl alcohol (qs) | AC |
|  | 20% KN128, 15% triacetin, 25% ethyl acetoacetate, isopropyl alcohol (qs) | AD |
| X07-055-11 | 20% KN128, 25% triacetin, 25% dipropylene glycol monomethyl ether, isopropyl alcohol (qs) | AE |
|  | 20% KN128, 25% benzyl alcohol, 25% dipropylene glycol monomethyl ether, isopropyl alcohol (qs) | AF |
|  | 20% KN128, 25% benzyl alcohol, 25% ethyl acetoacetate, isopropyl alcohol (qs) | AG |
| X07-055-12 | 20% KN128, 20% triacetin, 25% ethyl acetoacetate, isopropyl alcohol (qs) | AC |
|  | 20% KN128, 20% triacetin, 25% dipropylene glycol monomethyl ether, isopropyl alcohol (qs) | AH |
| X07-055-13 | 20% KN128, 20% triacetin, 25% dipropylene glycol monomethyl ether, isopropyl alcohol (qs) | AH |
| X07-055-14 | 20% KN128, 20% triacetin, 25% ethyl acetoacetate, isopropyl alcohol (qs) | AC |
| E07-118-01 | 150 mg/mL KN128, 479 mg/mL permethrin, ethyl acetoacetate (qs) | AI |
|  | 150 mg/mL KN128, 479 mg/mL permethrin, dipropylene glycol monomethyl ether (qs) | AJ |
|  | 150 mg/mL KN128, 479 mg/mL permethrin, benzyl alcohol, isopropyl alcohol (qs) | AK |
| E07-119-01 | 200 mg/mL KN128, 598 mg/mL permethrin, ethyl acetoacetate (qs) | AA |
|  | 200 mg/mL KN128, 598 mg/mL permethrin, dipropylene glycol monomethyl ether (qs) | AL |
|  | 200 mg/mL KN128, 598 mg/mL permethrin, benzyl alcohol, isopropyl alcohol (qs) | AM |

What is claimed is:

1. A local, topical, spot-on formulation for control of ectoparasites on a domestic animal comprising an ectoparasitically effective amount of Indoxacarb, a veterinarily acceptable carrier, and isopropyl alcohol; wherein the concentration of Indoxacarb in said formulation is at least 100 g/L; and wherein said veterinarily acceptable carrier comprises ethyl acetoacetate and triacetin.

2. The formulation of claim 1, further comprising a pesticide in addition to Indoxacarb.

3. The formulation of claim 2, wherein said pesticide is selected from the group consisting of insect growth regulator, organophosphate pesticide, carbamate pesticide, organochlorine pesticides, pyrethrin pesticide, pyrethroid pesticide, nicotine pesticide, neonicotinoid pesticide, copper-containing pesticide, anthelmintic agent, benzimidazole, salicylanilide, substituted phenol pesticide, pyrimidine pesticide, imidazothiazole pesticide, a *Bacillus thuringensis* toxin, chlorobenzilate, cyfluthrin, cypermethrin, dicofol, endosulfan, esfenvalerate, fenvalerate, lambda-cyhalothrin, methoxychlor, sulfur, cyclodiene, ryania, KT-199, and praziquantel.

4. The formulation of claim 2, wherein said pesticide is a pyrethroid pesticide.

5. The formulation of claim 4, wherein said pyrethroid pesticide is permethrin.

6. The formulation of claim 2, wherein said pesticide is a phenylpyrazole.

7. The formulation of claim 6, wherein said phenylpyrazole is fipronil.

8. The formulation of claim 1, wherein said formulation comprises
   15-25% Indoxacarb;
   15-25% triacetin;
   10-40% ethyl acetoacetate; and
   QS isopropyl alcohol.

9. The formulation of claim 1, wherein said formulation comprises
   20% Indoxacarb;
   20% triacetin;
   25% ethyl acetoacetate; and
   QS isopropyl alcohol.

10. The formulation of claim 1, wherein said veterinarily acceptable carrier further comprises one or more of an adjuvant, co-solvent, colorant, surfactant, spreading oil, antioxidant, light stabilizer or tackifier.

* * * * *

UNITED STATES PATENT AND TRADEMARK OFFICE
CERTIFICATE OF CORRECTION

PATENT NO. : 8,475,818 B2  
APPLICATION NO. : 12/439351  
DATED : July 2, 2013  
INVENTOR(S) : Frank Guerino et al.

Page 1 of 1

It is certified that error appears in the above-identified patent and that said Letters Patent is hereby corrected as shown below:

Title page, item (73), Assignee "E. I. de Pont de Nemours and Company, Wilmington, DE (US)" should be listed as --E. I. du Pont de Nemours and Company, Wilmington, DE (US)--.

Signed and Sealed this
Nineteenth Day of November, 2013

Teresa Stanek Rea
*Deputy Director of the United States Patent and Trademark Office*